United States Patent
Kent et al.

(10) Patent No.: US 11,660,452 B2
(45) Date of Patent: May 30, 2023

(54) SYSTEMS AND METHODS FOR PREDICTING BENEFICIAL SPINAL CORDS STIMULATION TEMPORAL PATTERNS

(71) Applicant: PACESETTER, INC., Sylmar, CA (US)

(72) Inventors: Alexander Kent, Moutain View, CA (US); Jeffery M. Kramer, San Francisco, CA (US)

(73) Assignee: Pacesetter, Inc., Sylmar, CA (US)

( * ) Notice: Subject to any disclaimer, the term of this patent is extended or adjusted under 35 U.S.C. 154(b) by 616 days.

(21) Appl. No.: 15/905,641

(22) Filed: Feb. 26, 2018

(65) Prior Publication Data
US 2019/0262610 A1    Aug. 29, 2019

(51) Int. Cl.
*A61N 1/36* (2006.01)
*A61B 5/00* (2006.01)
*A61B 5/24* (2021.01)
*A61N 1/05* (2006.01)

(52) U.S. Cl.
CPC ............ *A61N 1/36071* (2013.01); *A61B 5/24* (2021.01); *A61B 5/4836* (2013.01); *A61N 1/36062* (2017.08); *A61N 1/36135* (2013.01); *A61N 1/0553* (2013.01)

(58) Field of Classification Search
CPC .................................................. A61N 1/36071
USPC ......................................................... 607/46
See application file for complete search history.

(56) References Cited

U.S. PATENT DOCUMENTS

| 2006/0015153 A1* | 1/2006 | Gliner | A61N 1/3606 |
| | | | 607/45 |
| 2010/0292752 A1* | 11/2010 | Bardakjian | A61N 1/36064 |
| | | | 607/45 |
| 2012/0184801 A1* | 7/2012 | Simon | A61N 1/36025 |
| | | | 600/14 |
| 2014/0288620 A1* | 9/2014 | DiLorenzo | A61N 1/36053 |
| | | | 607/62 |
| 2014/0350634 A1* | 11/2014 | Grill | A61N 1/36139 |
| | | | 607/45 |
| 2015/0360031 A1 | 12/2015 | Bornzin et al. | |
| 2016/0121110 A1* | 5/2016 | Kent | A61B 5/7282 |
| | | | 607/45 |
| 2017/0173335 A1 | 6/2017 | Min et al. | |

* cited by examiner

Primary Examiner — Nicole F Lavert
(74) Attorney, Agent, or Firm — Norton Rose Fulbright US LLP (57) ABSTRACT

In one embodiment, the present disclosure is directed to a method for providing a neural stimulation therapy to treat chronic pain of a patient. The method comprises: recording, using a neural sensing system, neural activity of the patient at one or more sites within the nervous system of the patient related to the chronic pain of the patient, modifying a computational neural modeling system to model the sensed neural activity of the patient; computing a respective neural response of the patient for each of a plurality of different temporal stimulation patterns using the modified computational neural modeling system; selecting, based on the respective neural responses, one of the plurality of temporal stimulation patterns; and programming an implantable stimulation system to provide the selected one of the plurality of temporal stimulation patterns to the patient to treat the chronic pain of the patient.

17 Claims, 7 Drawing Sheets

SYSTEMS AND METHODS FOR PREDICTING BENEFICIAL SPINAL CORDS STIMULATION TEMPORAL PATTERNS

A. FIELD OF THE DISCLOSURE

The present disclosure relates generally to neurostimulation systems, and more particularly to predicting beneficial spinal cord stimulation temporal patterns using computational modeling systems.

B. BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders.

At least some known neurostimulation systems are closed-loop spinal cord stimulation (SCS) systems. These closed-loop SCS systems generally adjust stimulation settings based on neurological sensing systems.

However, in at least some known systems, selecting parameters for SCS relies on a "guess-and-check" approach to find therapeutically effective parameter sets for chronic pain. For example, for traditional tonic (i.e., continuous pulses) stimulation waveforms, there are several parameters that can be independently tuned, including stimulation amplitude, pulse width, frequency, and contact configuration (e.g., the location of cathodes and anodes). Moreover, with the introduction of other stimulation waveforms, such as burst stimulation, there are even more parameters to tune, including inter-burst and intra-burst frequency. Finally, it is also desirable to determine which stimulation waveform (tonic, burst, etc.) generates the best response in each individual patient. In at least some known systems, however, the process for selecting stimulation parameters may not be well-defined for efficiently and rationally identifying parameters that facilitate generating optimal therapy.

In tonic SCS, stimulation parameters may be adjusted until there is paresthesia coverage of painful regions of the patient's body. The stimulation amplitude generally determines the extent of neuronal activation. Accordingly, in at least some known systems, amplitude is titrated between a perception threshold (i.e., a level at which the patient senses paresthesia) and a discomfort threshold (i.e., a level at which the patient experiences discomfort). The discomfort threshold may be, for example, 1.4 to 1.7 times the perception threshold. In addition, pulse width and frequency may be adjusted. Increasing pulse width generally leads to smaller differences in stimulation thresholds between large and small diameter fibers. Increasing stimulation frequency generally leads to a higher rate of action potentials generation in activated spinal cord fibers.

In high-frequency SCS, a tonic waveform may be applied at frequencies in the 1 to 10 kilohertz (kHz) range to generate pain relief with reduced paresthesia. For example, for 10 kHz stimulation, amplitude may be 0.5 to 5 milliamps (mA) and pulse width may be 30 microseconds (µs). Paresthesia mapping is not generally used for high-frequency SCS, and instead, a stimulation site is more consistent, with stimulation typically applied at C4-C5 for chronic pain of the upper limbs/hands, and at T8-T12 for the back and lower limbs.

For burst SCS, a waveform including packets of high-frequency pulses that are separated by a quiescent period is used. Burst SCS often results in paresthesia-free stimulation. Typical waveform parameters may be, for example, a 500-1000 hertz (Hz) inter-burst frequency, a 40 Hz intra-burst frequency, five pulses per burst, and 0.5-1 millisecond (ms) pulse width. The amplitude is typically subsensory (e.g., 90% of the paresthesia threshold), and may average around 3.4 mA.

Accordingly, there are various SCS paradigms that use different temporal stimulation patterns to treat chronic pain. As described above, traditional patterns include low-frequency tonic stimulation, high-frequency tonic stimulation, and burst stimulation. Further, relatively new stimulation patterns have been developed, such as noise stimulation. In at least some known stimulation systems, a trial-and-error approach must be utilized to determine which stimulation therapy provides the most pain relief for a particular patient.

BRIEF SUMMARY OF THE DISCLOSURE

In one embodiment, the present disclosure is directed to a method for providing a neural stimulation therapy to treat chronic pain of a patient. The method comprises: recording, using a neural sensing system, neural activity of the patient at one or more sites within the nervous system of the patient related to the chronic pain of the patient, modifying a computational neural modeling system to model the sensed neural activity of the patient; computing a respective neural response of the patient for each of a plurality of different temporal stimulation patterns using the modified computational neural modeling system; selecting, based on the respective neural responses, one of the plurality of temporal stimulation patterns; and programming an implantable stimulation system to provide the selected one of the plurality of temporal stimulation patterns to the patient to treat the chronic pain of the patient.

In some embodiments, the neural activity corresponds to intrinsic neural activity in the absence of stimulation. In some embodiments, the neural activity corresponds to neural activity that occurs in response in stimulation at one or more frequencies.

In another embodiment, the present disclosure is directed to a method for dynamically adjusting spinal cord stimulation (SCS) applied to a patient. The method includes recording, using a neural sensing system, neural activity of the patient, inputting the recorded neural activity as a feedback signal into a closed-loop controller, and based on the feedback signal, adjusting SCS applied to the patient using the closed-loop controller.

In another embodiment, a computational modeling system for predicting beneficial spinal cord stimulation (SCS) temporal stimulation patterns is provided. The computational modeling system includes a processor, and a memory device communicatively coupled to the processor and storing computer-readable instructions that, when executed by the processor, cause the processor to: receive recorded neural activity for each of a plurality of SCS temporal stimulation patterns, the recorded neural activity recorded by a neural sensing system during application of each of the plurality of SCS temporal stimulation patterns to a patient; assess the impact of each temporal stimulation pattern, and select, based on the assessed impacts, one of the plurality of SCS temporal stimulation patterns.

The foregoing and other aspects, features, details, utilities and advantages of the present disclosure will be apparent

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for selecting beneficial spinal cord stimulation (SCS) or other neural stimulation temporal stimulation patterns. As used herein, a 'beneficial' spinal SCS temporal stimulation pattern refers to a pattern that facilitates optimizing analgesia (i.e., pain relief) while minimizing stimulation-related side effects. The methods include recording, using a neural sensing system, neural activity of a patient during application of each of a plurality of temporal stimulation patterns, inputting the recorded neural activity from each of the plurality of temporal stimulation patterns into a computational modeling system, assessing, using the computational modeling system, the impact of each temporal stimulation pattern, and selecting, based on the assessed impacts, one of the plurality of temporal stimulation patterns.

Neuropathic pain in patients often is a result of injury to neural tissue. The injury may be caused by a variety of events including mechanical injury, injury as a result of infection, and chemically induced changes as examples. Various patients' articulation of their chronic pain may be similar but the precise changes in neural activity caused by the damaged neural tissue may be different from patient to patient. The location of the damage and/or extent of the damage may vary from patient to patient and cause differences in the resulting pathological neural activity. Embodiments of the present disclosure attempt to optimize stimulation for patients by determining an optimal stimulation pattern to address an individual patient's pathological neural activity by modeling a portion of the individual's nervous system using analysis of observed neural activity and computational methods.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Under certain stimulation conditions, applying electrical energy to the spinal cord associated with regions of the body afflicted with chronic pain can induce "paresthesia" (a subjective sensation of numbness or tingling) in the afflicted bodily regions.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Figure 1:
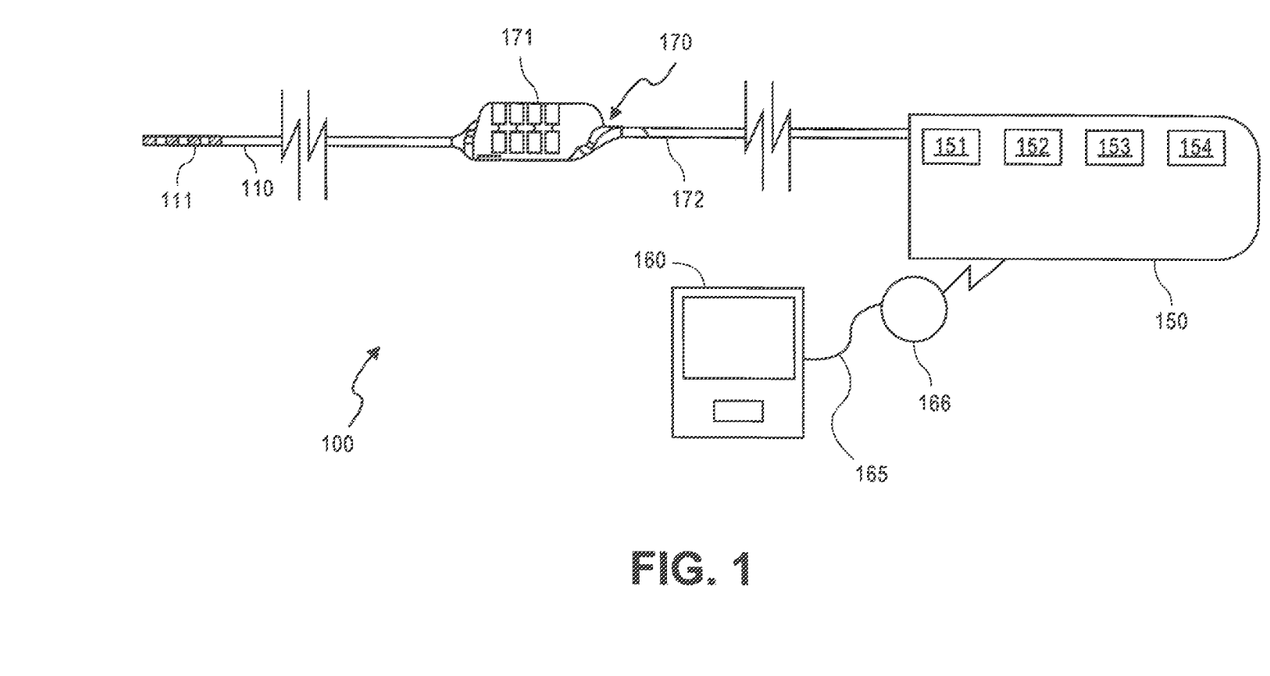
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. Stimulation system 100 includes an implantable pulse generator (IPG) 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of stimulation lead 110 and applied to tissue of a patient via electrodes 111. Any suitable known or later developed design may be employed for connector portion 171.

For implementation of the components within implantable pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of stimulation lead 110 to its distal end. The conductors electrically couple a plurality of electrodes 111 to a plurality of terminals (not shown) of stimulation lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
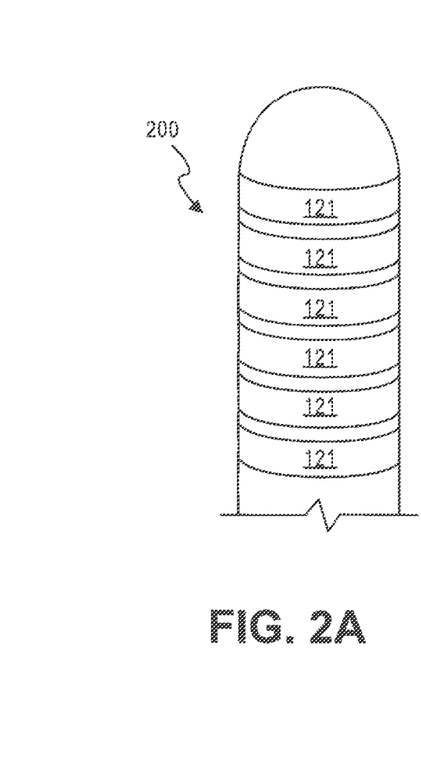
FIGS. 2A-2C are schematic views of stimulation portions that may be used with the stimulation system of FIG. 1.
Figure 2B:
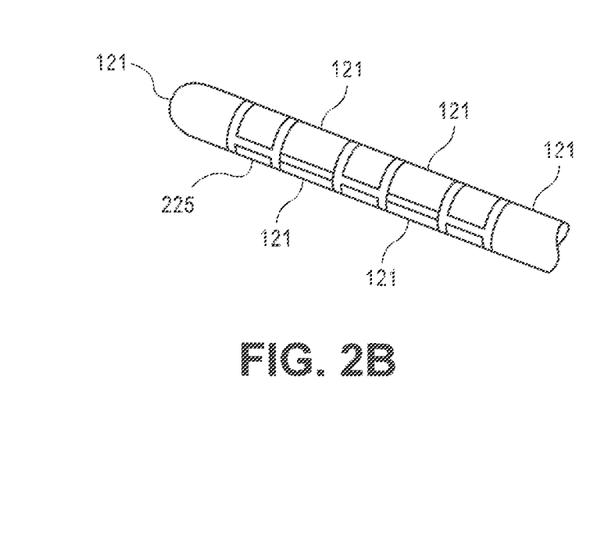
Figure 2C:
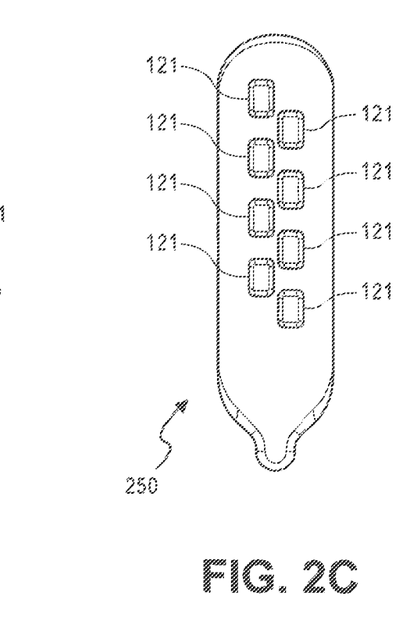

FIGS. 2A-2C respectively depict stimulation portions 200, 225, and 250 for inclusion at the distal end of stimulation lead 110. Stimulation portions 200, 225, and 250 each include one or more electrodes 121. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Controller device 160 (shown in FIG. 1) may be implemented to recharge battery 153 of implantable pulse generator 150 (although a separate recharging device could alternatively be employed). A "wand" 165 may be electrically connected to controller device 160 through suitable electrical connectors (not shown). The electrical connectors are electrically connected to a "primary" coil 166 at the distal end of wand 165 through respective wires (not shown). Typically, primary coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through primary coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of implantable pulse generator 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of implantable pulse generator 150 to be controlled by user after implantable pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with implantable pulse generator 150.

Controller device 160 preferably provides one or more user interfaces to allow the user to operate implantable pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Example commercially available neurostimulation systems include the PROCLAIM™ ELITE pulse generator and Clinician Programmer App from Abbott Laboratories. Example commercially available stimulation leads include the QUATTRODE™, OCTRODE™, AXXESS™, LAMITRODE™, TRIPOLE™, EXCLAIM™, and PENTA™ stimulation leads from Abbott Laboratories.

The systems and methods described herein facilitate determining a temporal stimulation pattern for a given patient to optimize or improve pain relief for that patient. As described herein, a neural sensing system is used to measure single-unit and/or compound action potential (CAP) activity from the patient's spinal cord during SCS. Further, a computational modeling system is used to determine how SCS alters firing rates throughout the spinal cord. The computational model may include representations of spinal neural circuitry and biophysical representations of individual neurons.

In one embodiment, measured neural activity from a patient is used as an input to the computational model, and the model is used to predict optimal SCS temporal pattern and stimulation parameters for that patient. In another embodiment, the computational model is applied to rapidly assess different SCS temporal patterns prior to clinical testing. In yet another embodiment, continuously measured neural activity is used as a feedback signal for a closed-loop controller to deliver stimulation when needed. Although SCS temporal patterns are analyzed according to some embodiments, stimulation patterns for other neural sites may be analyzed according to other embodiments. For example, dorsal root ganglion (DRG) stimulation may be analyzed according to embodiments of the disclosure. Also, neural activity may be measured and modeled in a variety of neural structures (including one or more dorsal root ganglia, dorsal roots, the spinal cord, dorsal horn, etc.) according to some embodiments.

In the embodiments described herein, a neural sensing system measures single-unit activity (i.e., neural activity from single neurons) and/or CAPs generated by near-synchronous activity of multiple neurons. In one embodiment, the neural sensing system is implemented using components of stimulation system 100 (shown in FIG. 1). The neural sensing system includes microelectrodes that record single-unit activity and/or macroelectrodes that record CAPs. Alternatively, it may be possible to use macroelectrodes to record single-unit activity. The macroelectrodes may be, for example, electrodes 111 on stimulation lead 110. The microelectrodes may be separate from stimulation lead 110, or may be connected to stimulation lead 110.

The microelectrodes and macroelectrodes are connected to suitable circuitry (e.g., amplifiers, filters, analog-to-digital converters, memory storage, microprocessors, etc.) for digital signal processing of the measured neural activity. This circuitry may be implemented, for example, within IPG 150 or within a separate, external system that is used while the terminal end of stimulation lead 110 is external to the patient.

Figure 3:
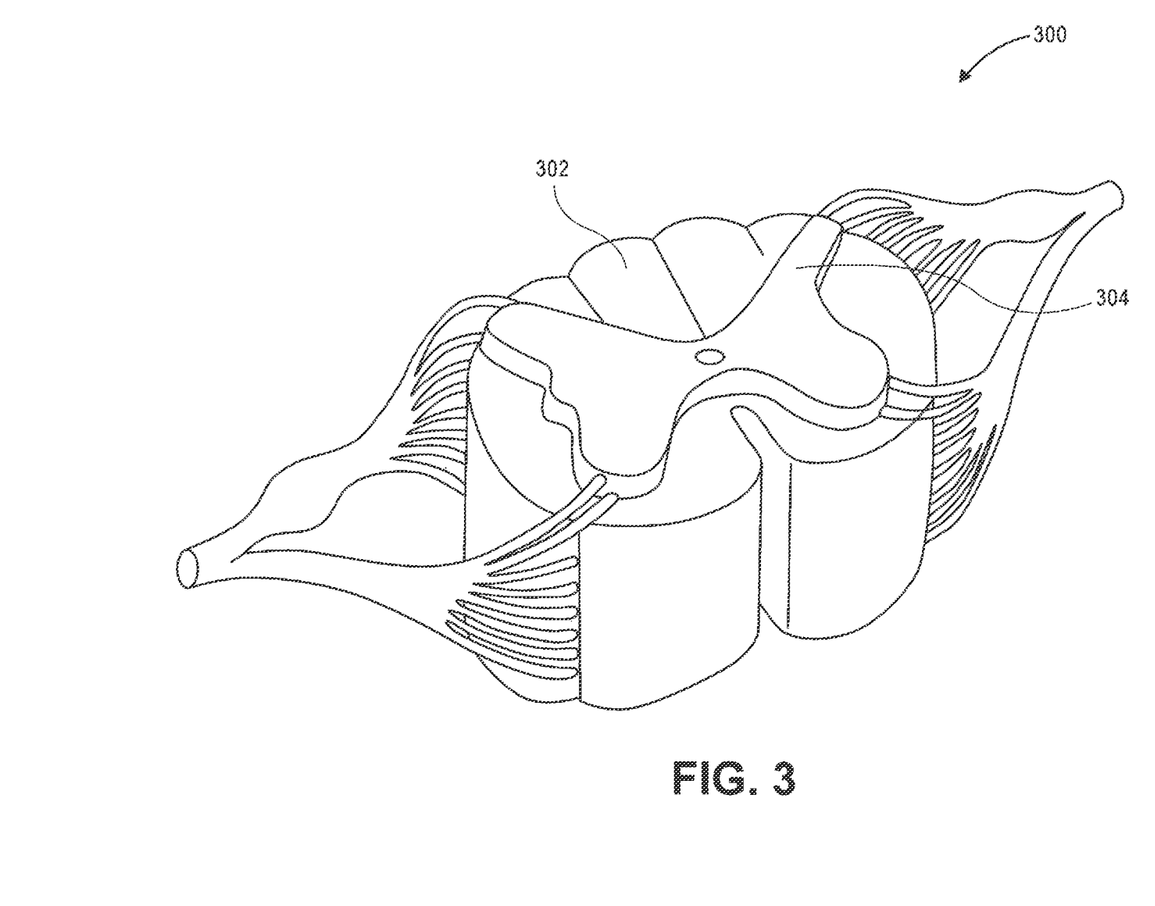
FIG. 3 is a schematic diagram of a portion of a spinal cord of a patient.

FIG. 3 is a schematic diagram of a portion of a spinal cord 300 of a patient. The neural sensing system described herein may record neural measurements from a dorsal column 302, dorsal horn 304, or from other structures in spinal cord 300.

The single-unit activity recorded may be analyzed to determine neuronal firing rates (e.g., action potentials per minute, in hertz (Hz)). The CAPs recorded may be analyzed to determine a total number of activated neurons (which is positively correlated to CAP peak magnitude), and the type(s) of active neurons. (e.g., large myelinated Aβ fibers, small myelinated Aδ fibers, and small unmyelinated C fibers).

Figure 4:
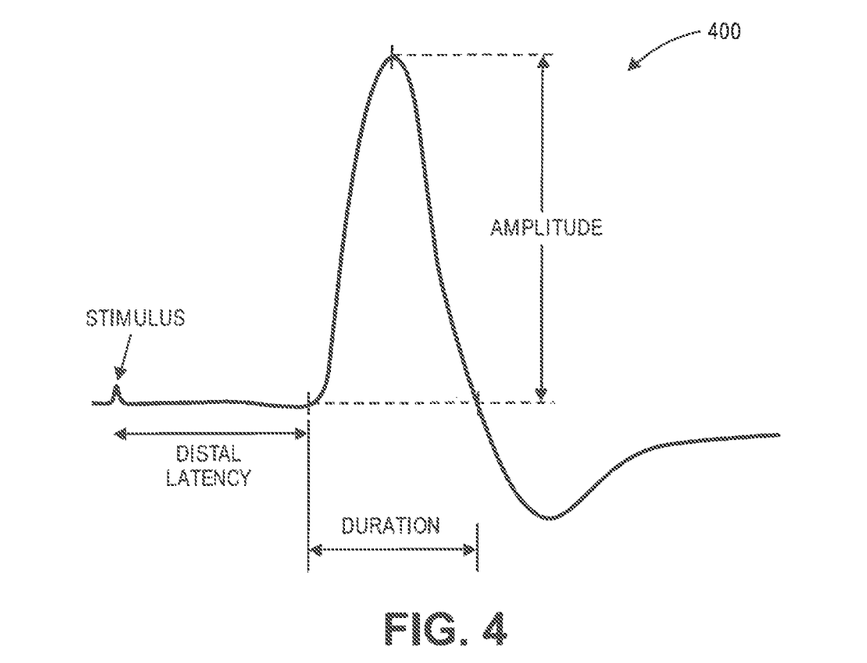
FIG. 4 is a plot of an example compound action potential (CAP).

FIG. 4 is a plot of an example CAP 400. As shown in FIG. 4, following stimulation, CAP 400 increases towards a peak after a distal latency period. CAP 400 has an amplitude and a duration, as shown in FIG. 4. The characteristics of CAP 400 indicate the type of active neuron. For example, larger fibers produce CAP peaks with shorter latency and shorter duration. In contrast, smaller fibers produce CAPs with longer latency and longer duration.

Figure 5:
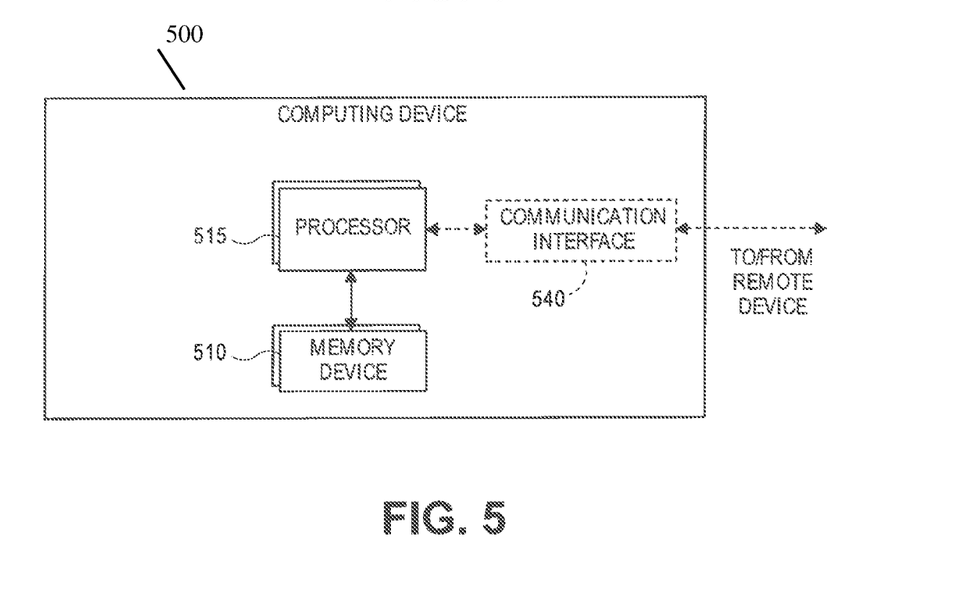
FIG. 5 is a block diagram of one embodiment of a computing device that may be used to apply a computational modeling system to neuronal activity recorded using a neural sensing system.

In the embodiments described herein, a computational modeling system is used to rapidly identify an optimal SCS temporal pattern for the patient, as described herein. FIG. 5 is a block diagram of one embodiment of a computing device 500 that may be used to implement the computational modeling system using neuronal activity recorded using the neural sensing system. Computing device 500 may be communicatively coupled (e.g., wired or wirelessly connected) to IPG 150.

In this embodiment, computing device 500 includes at least one memory device 510 and a processor 515 that is coupled to memory device 510 for executing instructions. In some embodiments, executable instructions are stored in memory device 510. In the illustrated embodiment, computing device 500 performs one or more operations described herein by programming processor 515. For example, processor 515 may be programmed by encoding an operation as one or more executable instructions and by providing the executable instructions in memory device 510.

Processor 515 may include one or more processing units (e.g., in a multi-core configuration). Further, processor 515 may be implemented using one or more heterogeneous processor systems in which a main processor is present with secondary processors on a single chip. In another illustrative example, processor 515 may be a symmetric multi-processor system containing multiple processors of the same type. Further, processor 515 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 510 is one or more devices that enable information such as executable instructions and/or other data to be stored and retrieved. Memory device 510 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 510 may be configured to store, without limitation, application source code, application object code, source code portions of interest, object code portions of interest, configuration data, execution events and/or any other type of data.

Computing device 500, in the illustrated embodiment, includes a communication interface 540 coupled to processor 515. Communication interface 540 communicates with one or more remote devices, such as a clinician or patient programmer. To communicate with remote devices, communication interface 540 may include, for example, a wired network adapter, a wireless network adapter, a radio-frequency (RF) adapter, and/or a mobile telecommunications adapter.

The computational modeling system applied by computing device 500 includes a representation of detailed spinal cord neural circuitry, in which different neuron types are appropriately distributed within different structures of the spinal cord, and which make excitatory or inhibitory synaptic connections with neurons in other areas. To facilitate maximizing simulation speeds, computing device 500 may be, for example, a multi-node server with high processing speeds and large memory capacity. In one embodiment, the output from computational modeling system is a firing rate of individual neurons throughout the spinal cord. Because of the network structure of the model, modulating neural activity in one area produces downstream changes in the neural activity of other areas in the spinal cord.

The computational modeling system may be, for example, the model described in "Mechanisms of dorsal column stimulation to treat neuropathic but not nociceptive pain: analysis with a computational model" by Arle, et al. (2014). However, those of skill in the art will appreciate that any suitable computational modeling system may be applied in the embodiments described herein.

Figure 6:
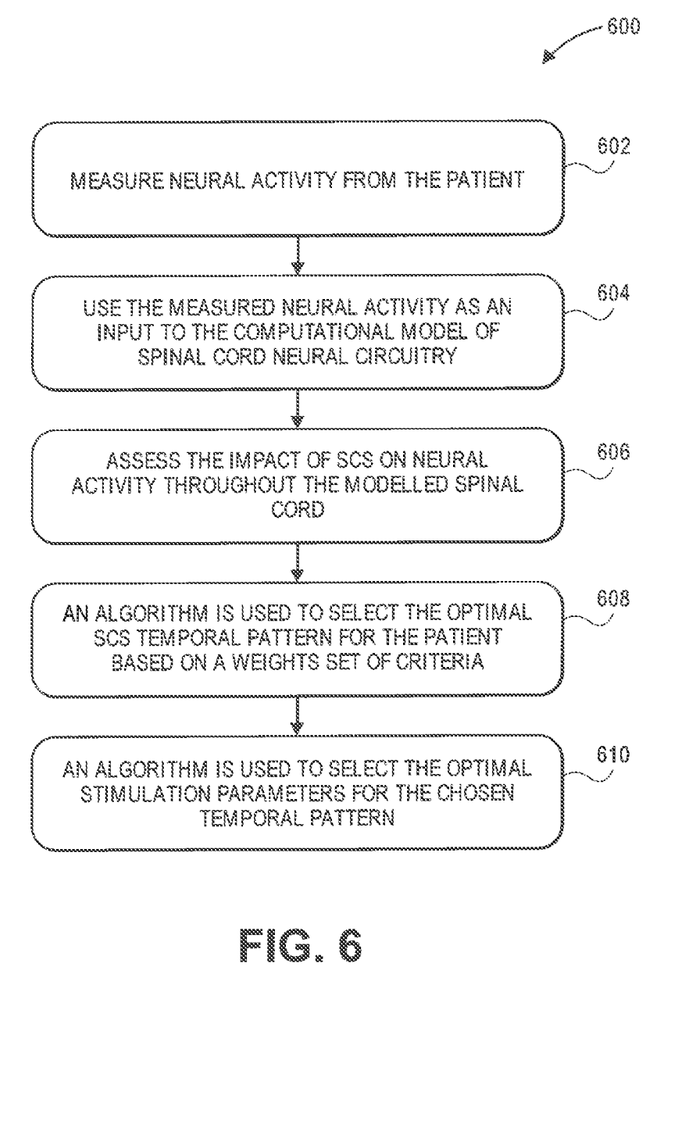
FIG. 6 is a flow chart of one embodiment of a method for using measured neural activity from a patient as an input to a computational modeling system to predict an optimal SCS temporal pattern.

FIG. 6 is a flow chart of one embodiment of a method 600 for using measured neural activity from the patient as an input to the computational modeling system to predict an optimal SCS temporal pattern. Method 600 may be implemented for a single patient or a group of patients with common characteristics. In method 600, neural activity 602 is measured from specific spinal cord structures of the patient (e.g., the dorsal column, dorsal horn, dorsal root entry zone (DREZ), and/or Lissauer tract). The neural activity is measured 602. The neural activity 602 may be intrinsic neural activity (i.e., in the absence of applied stimulation) for some embodiments. Alternatively, the neural activity 602 may be measured in response to stimulation at one or more frequencies for other embodiments.

The measured neural activity is used 604 as an input to the computational modeling system. That is, the computational modeling system includes parameters defining the firing rate of neurons at one or more locations within the modeled portion of the patient's nervous system. The corresponding parameters for the respective neurons in the computational model are set to fire at the rate determined by the actual firing rate of the observed neurons. In some embodiments, multiple firing rate parameters are calculated from analysis of neural activity of the patient. Respective firing rate parameters may correspond to different neural fiber types and/or different locations within the modeled portion of the patient's nervous system. Moreover, the type and number of neurons that fire in the model correspond to that of the observed neurons. Then, using the computational modeling system, the impact of each temporal stimulation pattern on neural activity throughout the modelled spinal cord is assessed 606.

Based on the output of the model, in this embodiment, an algorithm is applied to select 608 the optimal temporal stimulation pattern for the patient. Specifically the algorithm determines which delivered temporal stimulation pattern best satisfies predetermined criteria. The criteria may, in some embodiments, be weighted differently from one another.

For example, in one embodiment, the algorithm may evaluate each temporal stimulation pattern based on the following criteria: i) reduce neuropathic pain transmission by minimizing the firing rate and number of activated wide dynamic range (WDR) neurons in lamina V of the dorsal horn, ii) reduce paresthesia sensations by minimizing the firing rate and number of activated $A\beta$ nerve fibers in the dorsal column, and iii) improve battery life by minimizing stimulation power, which is generally a function of stimulation amplitude, pulse width, frequency, and duty cycle. Alternatively, the algorithm may evaluate each temporal stimulation pattern based on any suitable criteria.

Once an optimal temporal stimulation pattern is selected 608, optimal stimulation parameters (e.g., amplitude, frequency, pulse width, duty cycle, and contact configuration (i.e., which electrodes 111 are activated and which are not)) may be selected 610 using the computational model.

Method 600 may be performed during initial SCS programming and/or performed periodically to maintain optimal therapy for the patient over time. When performing method 600 periodically, machine learning algorithms may be implemented help determine optimal settings for the patient. For example, a machine learning algorithm may be trained using the measured neural activity, outputs from the computational model, and data collected periodically from the patient regarding pain relief obtained from delivered stimulation. Other inputs to the machine learning algorithm may include, for example, time of day and patient activity level during application of stimulation. Subsequently, the machine learning algorithm may assist in selecting optimal stimulation settings based on the present situation.

Figure 7:
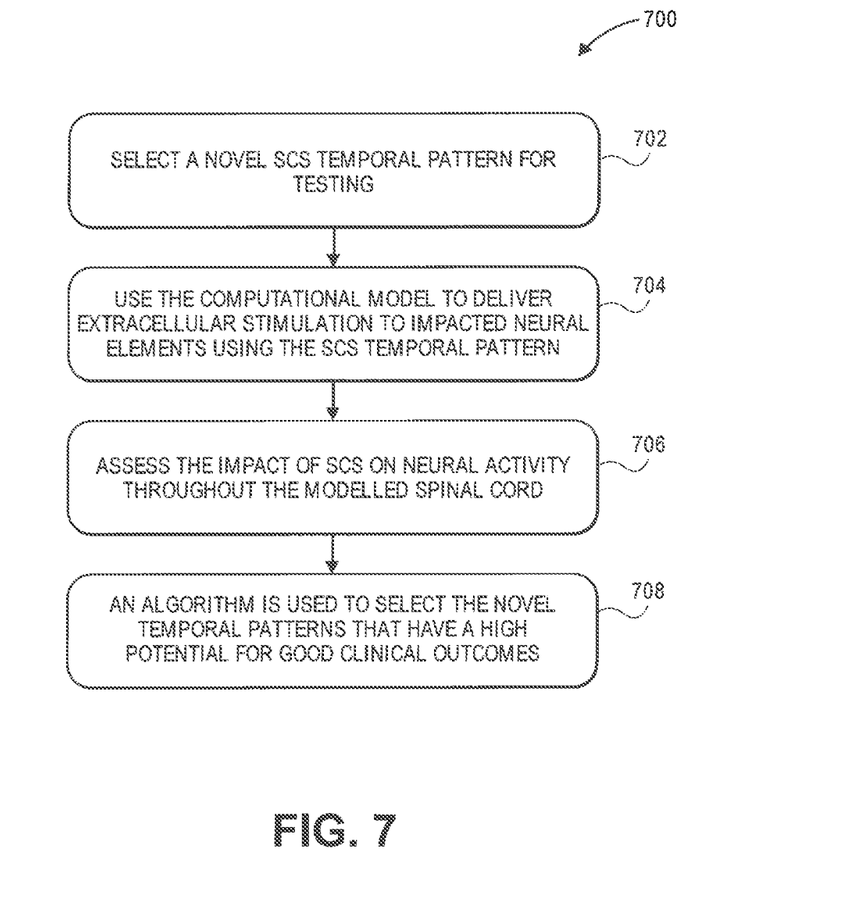
FIG. 7 is a flow chart of one embodiment of a method for assessing temporal stimulation patterns using a computational modeling system.

FIG. 7 is a flow chart of one embodiment of a method 700 for assessing temporal stimulation patterns (e.g., novel stimulation patterns other than tonic stimulation, high-frequency stimulation, burst stimulation, and noise stimulation) using the computational model. Initially, a temporal stimulation pattern to be evaluated is selected 702. Notably, in method 700, measured neural activity from patients is not available as an input to the computational model. Accordingly, in this embodiment, generic neural activity from historical patient data (e.g., average patient data) or from academic publications is used as the input to the computational model. The general neural activity is intrinsic neural activity without stimulation being applied.

Subsequently, the computational model is used to "deliver" 704 extracellular stimulation to the modelled neural elements that are likely to be impacted by the temporal stimulation pattern (e.g., dorsal column fibers). That is, the computational model simulates the temporal stimulation pattern of interest. The impact of the extracellular stimulation is assessed 706 throughout the modelled spinal cord. Steps 702-706 can be repeated for any number of temporal stimulation patterns of interest. An algorithm is then used 708 to select stimulation patterns that achieve criteria that indicate a relatively high potential for good clinical outcomes. For example, the algorithm may be used 708 to select temporal stimulation patterns that minimize activity of WDR in lamina V of the dorsal horn and that minimize activity of $A\beta$ nerve fibers in the dorsal column.

Figure 8:
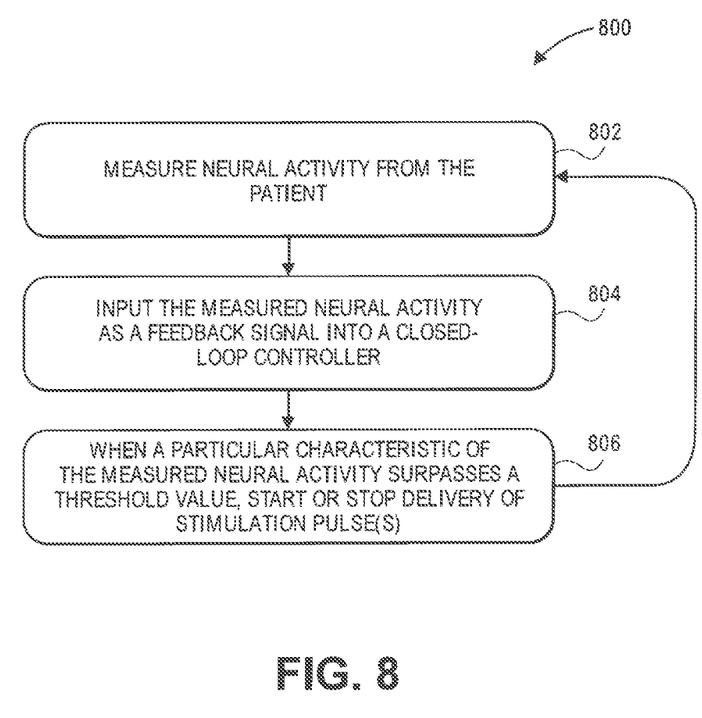
FIG. 8 is a flow chart of one embodiment of a method for using measured neural activity as a feedback signal for automatic adjustment of a continuously modulating temporal stimulation pattern.

FIG. 8 is a flow chart of one embodiment of a method 800 for using measured neural activity as a feedback signal for automatic adjustment of a continuously modulating temporal stimulation pattern. Using method 800, SCS is delivered to the patient as needed. In contrast to methods 600 and 700, method 800 does not utilize the computational modeling system. Specifically, neural activity of the patient is measured 802 (e.g., using the neural sensing system described herein). The measured neural activity is subsequently input 804 as a feedback signal into a closed-loop controller (e.g., controller 151 (shown in FIG. 1)). Based on the feedback signal, the closed-loop controller controls when stimulation pulses or groups of pulses are delivered to optimize stimulation for the current state of neural activity.

In this embodiment, the closed-loop controller selectively stops or starts 806 delivery of stimulation pulses when a particular characteristic of the measured neural activity exceeds a predetermined threshold. For example, the closed-loop controller may deliver a specified number of pulses whenever a firing rate of WDR neurons in the dorsal horn exceeds a predetermined threshold, which would be indicative of increased pain transmission. In another example, the closed-loop controller may temporarily discontinue stimulation if activity in the dorsal column exceeds a predetermined threshold, which would be indicative of generation of paresthesia sensations. The neural activity is again measured 802 after the closed-loop controller adjusts stimulation.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for providing a neural stimulation therapy to treat chronic pain of a patient, comprising:
recording, using a neural sensing system, neural activity data of the patient at one or more sites within a nervous system of the patient related to the chronic pain of the patient; modifying a computational neural modeling system to model the neural activity data of the patient, wherein the computational neural modeling system is configured to generate an output corresponding to a firing rate of individual neurons positioned within a spinal cord of the patient, wherein the modifying comprises measuring one or more frequencies of the sensed neural activity data and assigning one or more firing rate parameters in the computational neural modeling system to values selected according to the one or more measured frequencies; assessing a respective neural response of the patient for each of a plurality of different temporal stimulation patterns using the modified computational neural modeling system; selecting, based on the respective neural responses, one of the plurality of different temporal stimulation patterns; and programming an implantable stimulation system to provide the selected one of the plurality of different temporal stimulation patterns to the patient to treat the chronic pain of the patient.

2. The method of claim 1 wherein at least one frequency assigned to a firing rate parameter of the computational neural modeling system is determined by measuring neural activity in the patient that occurs in response to application of trial stimulation pulses to the patient.

3. The method of claim 1, wherein the recording the neural activity data comprises measuring neural activity of a single neuron and measuring compound action potentials (CAPs) of multiple neurons.

4. The method of claim 1, wherein the recording the neural activity data comprises measuring neural activity from specific spinal cord structures of the patient.

5. The method of claim 1, wherein the neural activity data corresponds to one of intrinsic neural activity and neural activity generated in response to an applied stimulation.

6. The method of claim 1, wherein the selecting the one of the plurality of different temporal stimulation patterns comprises selecting a pulse amplitude and a pulse width corresponding to the one of the plurality of different temporal stimulation patterns.

7. The method of claim 6, wherein the selecting the one of the plurality of different temporal stimulation patterns comprises selecting a pulse frequency and a pulse repetition parameter corresponding to the one of the plurality of different temporal stimulation patterns.

8. The method of claim 1, wherein the assessing the respective neural response of the patient comprises evaluating each of the plurality of different temporal stimulation patterns based on an extent to which a temporal stimulation pattern of the plurality of different temporal stimulation patterns reduces at least one of neuropathic pain transmission and paresthesia sensations.

9. The method of claim 8, wherein the assessing the respective neural response of the patient comprises evaluating each of different plurality of the temporal stimulation patterns based on an extent to which a temporal stimulation pattern of the plurality of different temporal stimulation patterns extends a life of a battery of the implantable stimulation system.

10. A method for providing a neural stimulation therapy to treat chronic pain of a patient, comprising:
recording, using a neural sensing system, neural activity data of the patient at one or more sites within a nervous system of the patient related to the chronic pain of the patient, the neural activitydata corresponding to intrinsic neural activity in the absence of stimulation, wherein the neural activity data comprises first neural activity recorded at individual neurons and second neural activity recorded at multiple neurons, and wherein the second neural activity corresponds to near-synchronous activity; modifying a computational neural modeling system to model the sensed neural activitydata of the patient, wherein the computational neural modeling system is configured to generate an output corresponding to a firing rate of individual neurons positioned within a spinal cord of the patient; computing a respective neural response of the patient for each of a plurality of different temporal stimulation patterns using the modified computational neural modeling system; selecting, based on the respective neural responses, one of the plurality of different temporal stimulation patterns; and programming an implantable stimulation system to provide the selected one of the plurality of different temporal stimulation patterns to the patient to treat the chronic pain of the patient.

11. The method of claim 10, further comprising delivering electric pulses to the one or more sites within the nervous system of the patient, wherein the electric pulses include parameters corresponding to the selected one of different plurality of the temporal stimulation patterns.

12. The method of claim 10, wherein the selected one of the plurality of different temporal stimulation patterns comprises a temporal stimulation pattern having a particular amplitude, pulse width, and duty cycle.

13. A device for providing neural stimulation therapy to treat chronic pain of a patient, the device comprising: electrodes configured to record neural activity data corresponding to neural activity of the patient at one or more sites within a nervous system of the patient and related to the chronic pain of the patient, wherein the electrodes configured to record the neural activity data comprise microelectrodes configured to record the neural activity data generated at single neurons and macroelectrodes configured to record the neural activity data generated by near-synchronous activity of multiple neurons; and an implantable pulse generator coupled to the electrodes and configured to: send the neural activity data to a computing device configured to store a biophysical model of neurons, wherein the biophysical model of neurons is configured to generate an output corresponding to a firing rate of individual neurons positioned within a spinal cord of the patient; receive a temporal stimulation program selected at the computing device from among a plurality of temporal stimulation pattern programs; and stimulate the nervous system of the patient based on the temporal stimulation program.

14. The device of claim 13, wherein the implantable pulse generator is communicatively coupled to the computing device.

15. The device of claim 13, wherein the implantable pulse generator is configured to:
   generate an electrical pulse having an amplitude, a frequency, a width, and a repetition parameter corresponding to the temporal stimulation program; and
   transmit the electrical pulse to the electrodes.

16. The device of claim 15, wherein the electrodes are further configured to transmit the electrical pulse to the one or more sites within the nervous system of the patient, and wherein the one or more sites correspond to a spinal cord of the patient.

17. The device of claim 13, wherein the individual neurons are located within a spinal cord of the patient.

* * * * *

UNITED STATES PATENT AND TRADEMARK OFFICE
CERTIFICATE OF CORRECTION

PATENT NO. : 11,660,452 B2
APPLICATION NO. : 15/905641
DATED : May 30, 2023
INVENTOR(S) : Alexander Kent et al.

Page 1 of 1

It is certified that error appears in the above-identified patent and that said Letters Patent is hereby corrected as shown below:

In the Claims

At Column 12, Claim number 10, Line number 65, delete "activitydata" and replace with --activity data--.
At Column 13, Claim number 10, starting at Line number 5, delete "activitydata" and replace with --activity data--.

Signed and Sealed this
Eighteenth Day of July, 2023

Katherine Kelly Vidal
*Director of the United States Patent and Trademark Office*